(12) United States Patent
Wang et al.

(10) Patent No.: US 12,019,071 B2
(45) Date of Patent: Jun. 25, 2024

(54) COMPOSITION AND METHODS FOR EXTRACTING MYCOTOXINS

(71) Applicant: Waters Technologies Corporation, Milford, MA (US)

(72) Inventors: Xinwen Wang, Bedford, MA (US); Jianmin Liu, Framingham, MA (US); Stephen P. Powers, Upton, MA (US)

(73) Assignee: Waters Technologies Corporation, Milford, MA (US)

( * ) Notice: Subject to any disclaimer, the term of this patent is extended or adjusted under 35 U.S.C. 154(b) by 146 days.

(21) Appl. No.: 15/570,540

(22) PCT Filed: Oct. 29, 2015

(86) PCT No.: PCT/US2015/044646
§ 371 (c)(1),
(2) Date: Oct. 30, 2017

(87) PCT Pub. No.: WO2016/182589
PCT Pub. Date: Nov. 17, 2016

(65) Prior Publication Data
US 2018/0149649 A1    May 31, 2018

Related U.S. Application Data

(60) Provisional application No. 62/159,019, filed on May 8, 2015.

(51) Int. Cl.
| | |
|---|---|
| *C07K 1/14* | (2006.01) |
| *C07K 14/37* | (2006.01) |
| *G01N 33/53* | (2006.01) |
| *G01N 33/569* | (2006.01) |
| *G01N 33/94* | (2006.01) |

(52) U.S. Cl.
CPC ......... *G01N 33/56961* (2013.01); *C07K 1/14* (2013.01); *C07K 14/37* (2013.01); *G01N 33/5308* (2013.01); *G01N 33/94* (2013.01); *G01N 2333/37* (2013.01); *G01N 2333/38* (2013.01)

(58) Field of Classification Search
CPC ............. G01N 33/56961; G01N 33/94; G01N 2333/37; G01N 2333/38; G01N 33/5308; G01N 3/56961; C07K 14/37; C07K 1/14
See application file for complete search history.

(56) References Cited

U.S. PATENT DOCUMENTS

| | | | |
|---|---|---|---|
| 2004/0185051 A1* | 9/2004 | Schmechel | C07K 16/14 424/152.1 |
| 2009/0081808 A1 | 3/2009 | Burmeister et al. | |
| 2011/0060131 A1* | 3/2011 | Barile | C12N 9/1241 530/389.8 |
| 2011/0159121 A1* | 6/2011 | McDaniel | A61K 8/97 424/727 |
| 2011/0281283 A1* | 11/2011 | Moran | C07K 16/14 435/7.31 |
| 2012/0034711 A1 | 2/2012 | Li et al. | |

FOREIGN PATENT DOCUMENTS

| | | | | |
|---|---|---|---|---|
| CN | 101812121 B | * | 6/2013 | |
| JP | 2012-220401 A | | 11/2012 | |
| WO | 9932886 A1 | | 7/1999 | |
| WO | WO-2005118841 A1 | * | 12/2005 | ............... C12Q 1/25 |
| WO | WO-2006066804 A1 | * | 6/2006 | ......... G01N 33/5038 |
| WO | 2013-116847 A1 | | 8/2013 | |
| WO | WO-2014018195 A1 | * | 1/2014 | ........... C12Q 1/6806 |

OTHER PUBLICATIONS

Trucksess et al. Determination of Aflatoxins and Ochratoxin A in Ginseng and Other Botanical Roots by Immunoaffinity Column Cleanup and Liquid Chromatography with Fluorescence Detection. J. AOAC Int. 2006, vol. 89, Issue 3, pp. 624-630. (Year: 2006).*
Maragos et al. Extraction of Aflatoxins Bi and Gi from Maize by Using Aqueous Sodium Dodecyl Sulfate. Journal of AOAC Int. 2008, vol. 91, No. 4, pp. 762-765. (Year: 2008).*
International Search Report issued in PCT/US2015/044646, dated Oct. 20, 2015.
Maragos, "Extraction of aflatoxins B1 and G1 from maize by using aqueous sodium dodecyl sulfate," Journal of AOAC International, vol. 91, No. 4, pp. 762-767 (2008).
Anfossi, L., et al: "Development of a quantitative lateral flow immunoassay for the detection of aflatoxins in maize", Food Additives & Contaminants: Part A., 28 (2): 226-234 (2011).
Bokhari, F., "Implications of fungal infections and mycotoxins in camel diseases in Saudi Arabia", Saudi Journal of Biological Sciences, 17(1): 73-81 (2010).
Pimentel, M.C.B., et al: "Aqueous two-phase system for citrinin extraction from fermentation broth", Separation and Purification Technology, 110: 158-163 (2013).
Supplementary European Search Report for EP15892044 dated Oct. 10, 2018.
Author unknown, "Food Safety Inspection Technology", Wang Shipping, China Agricultural University Press, (2009) 6 pages.
Chinese Office Action for Application No. 201580081460.4, dated Aug. 5, 2020, original and translated document combined, 23 pages.

* cited by examiner

*Primary Examiner* — Shafiqul Haq
(74) *Attorney, Agent, or Firm* — WOMBLE BOND DICKINSON (US) LLP; Deborah M. Vernon (57) ABSTRACT

Disclosed is a composition for extracting mycotoxins or aflatoxins from a food sample. The methods using the composition to detect and analyze the aflatoxins are also provided.

8 Claims, 3 Drawing Sheets

FIG. 1

```
┌─────────────────────────────┐
│   5g Peanut / Peanut paste  │
└──────────────┬──────────────┘
               ▼
┌─────────────────────────────────────────────────┐
│ 15mL H2O +                                      │
│ 5mL First Liquid Concentrate of the Invention + │
│ 5mL Second Liquid Concentrate of the Invention  │
└──────────────────────┬──────────────────────────┘
                       ▼
         ┌─────────────────────────┐
         │   Vortex for 2 minutes  │
         └────────────┬────────────┘
                      ▼
         ┌─────────────────────────┐
         │ Go through fluted filter paper │
         └────────────┬────────────┘
                      ▼
         ┌─────────────────────────┐
         │  Add 100ul to Afla-V strip │
         └────────────┬────────────┘
                      ▼
         ┌─────────────────────────┐
         │   Develop for 5 minutes │
         └────────────┬────────────┘
                      ▼
              ┌──────────────┐
              │  Read strip  │
              └──────────────┘
```

COMPOSITION AND METHODS FOR EXTRACTING MYCOTOXINS

CROSS-REFERENCE TO RELATED APPLICATIONS

This application is a 35 U.S.C. § 371 National Phase Application of International PCT Patent Application No. PCT/US2015/044646, filed Oct. 29, 2015 which application claims the benefit of and priority to U.S. Provisional Application Nos. 62/036,410 filed on Aug. 12, 2014 and 62/159,019 filed May 8, 2015. The entire contents of these applications are incorporated herein by reference in their entirety.

FIELD OF THE INVENTION

The present invention provides a composition for extracting mycotoxins from a sample and a method of extracting mycotoxins using the composition. Particularly, the method using the composition of the invention provides efficient extraction of mycotoxins such as aflatoxins without using an organic solvent.

BACKGROUND OF THE INVENTION

Awareness of the incidence and effect of human and animal exposure to toxic substances by humans and other animals via food, water, and air is of critical importance to our survival.

Aflatoxins are a typical example of the compounds for which screening is desired. Aflatoxins are naturally occurring toxins of secondary fungal metabolites. These mycotoxins are produced by *Aspergillus flavus* or *Aspergillus parasiticus*. In the food industry, aflatoxins are also detected in produce such as peanuts, peanut meal, cottonseed meal, corn, dried chili peppers, and the like. These mycotoxins are frequent contaminants of the human food supply in many areas of the world and are statistically associated with increased incidence of human liver cancer in Asia and Africa, in particular. Therefore, aflatoxins can cause significant losses in the food industry.

As such, in the food industry, the detection and quantification procedures for mycotoxins such as aflatoxin, ochratoxin, zearalenone and fumonisin have become particularly important in accordance with strengthened regulations on produce and food products. Currently, for example, commercially available affinity columns have been used for detecting the presence of mycotoxins or particularly for detecting aflatoxins.

In commercially available methods, organic solvents have been generally used to extract such mycotoxins from the sample. Since mycotoxins such as aflatoxin, fumonisin, ochratoxin, zearalenone and the like have multiple-aromatic rings or long-hydrophobic chains in their structures, use of organic solvents has been preferred for efficient extracting and accurate profiling of such mycotoxins in samples. However, organic solvents such as methanol or ethanol are flammable, toxic, and require extra expenditure for storage and disposal as hazardous waste. Accordingly, a need for extracting mycotoxins or aflatoxins from commodity samples without use of organic solvents has emerged.

SUMMARY OF THE INVENTION

The present invention provides technical solutions to the currently used methods of detecting mycotoxins from food samples using organic solvents. Accordingly, in the present invention, a composition for effective extraction of mycotoxins from a sample without using an organic solvent is disclosed. Further, the methods of detecting mycotoxins using the composition of the invention are disclosed.

In one aspect, the present invention provides a composition for extracting mycotoxins in a sample. The composition may comprise: one or more of surfactants; one or more of polymers; one or more of viscosity modifiers; and one or more of buffering salts.

In another aspect, the present invention provides a first concentrated liquid and a second concentrated liquid for extracting mycotoxins in a sample. The first and second concentrated liquids may independently comprise: one or more of surfactants; one or more of polymers; one or more of viscosity modifiers; and one or more of buffering salts.

In certain exemplary embodiments, the surfactant may be selected from the group consisting of polysorbate 20 (Tween 20), sodium stearate, 4-(5-dodecyl) benzenesulfonate, sodium dodecyl sulfate (SDS), and trimethylhexadecyl ammonium chloride.

In yet certain exemplary embodiments, the polymer may be selected from the group consisting of polyacrylic acid, polyol, polyethylene glycol (PEG), and polyvinylpyrrolidone.

In other certain exemplary embodiments, the viscosity modifier may be selected from the group consisting of sucrose, cellulose, mannitol and combinations thereof.

In certain embodiments, the buffering salt may be a salt, an acidic salt, a basic salt or combinations thereof. In certain exemplary embodiments, the buffering salt may be one or more selected from the group consisting of sodium chloride, sodium sulfate, sodium citrate, sodium acetate, sodium bromide, sodium iodide, potassium chloride, potassium acetate, potassium bromide, and potassium iodide, sodium bicarbonate, sodium hydrosulfide, sodium bisulfate, monosodium phosphate, disodium phosphate, calcium carbonate, sodium carbonate, potassium cyanide, and sodium sulfide.

In certain exemplary embodiments, the surfactant may be included in an amount of about 2 to 10 wt % based on the total amount of the composition. In addition, the polymer may be included in an amount of about 30 to 50 wt % based on the total amount of the composition. Further, the viscosity modifier may be included in an amount of about 30 to 50 wt % based on the total amount of the composition. The buffering salt may be included in an amount of about 10 to 18 wt % based on the total amount of the composition.

In other exemplary embodiments, the surfactant may be included in an amount of about 2.4 and 7.2 wt % of the first concentrated liquid and 5 to 15% volume % of the second concentrated liquid. Buffering salts may be included in an amount of 6 to 18 wt % and 1.4 to 4.2 wt % in the second concentrated liquid based on the total amount of the concentrated liquid. In certain embodiments, polymer may be included in an amount of about 30 to 50 wt % based on the total amount of the composition.

In an exemplary embodiment, the composition of the present invention may consist of, or consist essentially of: sodium dodecyl sulfate (SDS) in an amount of about 6 wt %; polyethylene glycol (PEG) in an amount of about 40 wt %; sucrose in an amount of about 40 wt %; sodium chloride (NaCl) in an amount of about 7 wt %; and sodium dihydrogenphosphate ($NaH_2PO_4$) in an amount of about 7 wt %, based on the total weight of the composition.

In an exemplary embodiment, the first and second concentrated liquids of the present invention may consist of, or consist essentially of aqueous solutions of: sodium dodecyl sulfate (SDS) in an amount of about 4.8 wt %; sodium chloride (NaCl) in an amount of about 12.4 wt %; polysorbate 20 in an amount of 10 volume %; and sodium dihydrogenphosphate (NaH2PO4) in an amount of about 2.8 wt %, based on the total weight of the composition.

In other aspect, provided is a method of detecting mycotoxins from a sample.

In an exemplary embodiment, the method may comprise: preparing the sample by combining with a composition of the invention; and extracting the mycotoxins from the prepared sample.

In certain exemplary embodiments, the composition of the invention used in the methods may comprise: sodium dodecyl sulfate (SDS) in an amount of about 6 wt %; polyethylene glycol (PEG) in an amount of about 40 wt %; sucrose in an amount of about 40%; sodium chloride (NaCl) in an amount of about 7 wt %; and sodium dihydrogenphosphate ($NaH_2PO_4$) in an amount of about 7 wt %, based on the total weight of the composition.

In another exemplary embodiment, the method may comprise: preparing the sample by combining with a first and a second concentrated liquid of the invention; and extracting the mycotoxins from the prepared sample. In certain embodiments, the sample is prepared in water. In particular embodiments, the sample is prepared by addition of water prior to addition of the first and second concentrated liquids.

In certain exemplary embodiments, the first concentrated liquid of the invention used in the methods may comprise: sodium dodecyl sulfate (SDS) in an amount of about 4.8 wt %; In certain exemplary embodiments, the second concentrated liquid of the invention used in the methods may comprise: Polysorbat 20 in an amount of 10 volume %: sodium chloride (NaCl) in an amount of about 12.4 wt %; and sodium dihydrogenphosphate ($NaH_2PO_4$) in an amount of about 2.8 wt %, based on the total weight of the composition.

In certain exemplary embodiments, the samples may be prepared as an aqueous solution.

In certain exemplary embodiments, the extracting may be performed by vortexing for about 2 min.

In certain embodiments, the method may further comprise filtering the prepared sample.

In yet certain embodiments, the method may further comprise analyzing the mycotoxins from the sample. In certain exemplary embodiments, the mycotoxins may be analyzed by a test strip which includes affinity tags having specificity to the mycotoxins. Exemplary mycotoxins analyzed in the methods of the present invention may be, but not limited to, aflatoxins. In particular, when the aflatoxins are analyzed, the test strip may be AFLA-V® strip (VICAM, Milford, MA).

In still certain embodiments, the method may further comprise quantitating the amount of the mycotoxins from the sample. In certain exemplary embodiments, the amount of the mycotoxins may be quantitated by measuring a fluorescence at wavelength of about 454 nm in a single-cell fluorometer.

In another aspect, the present invention also provides a kit which may comprise: the composition of the invention, an affinity test strip, and instructions for use. In particular, the kit may include the affinity test strip of AFLA-V® strip (VICAM, Milford, MA).

DETAILED DESCRIPTION OF THE INVENTION

Figure 1:
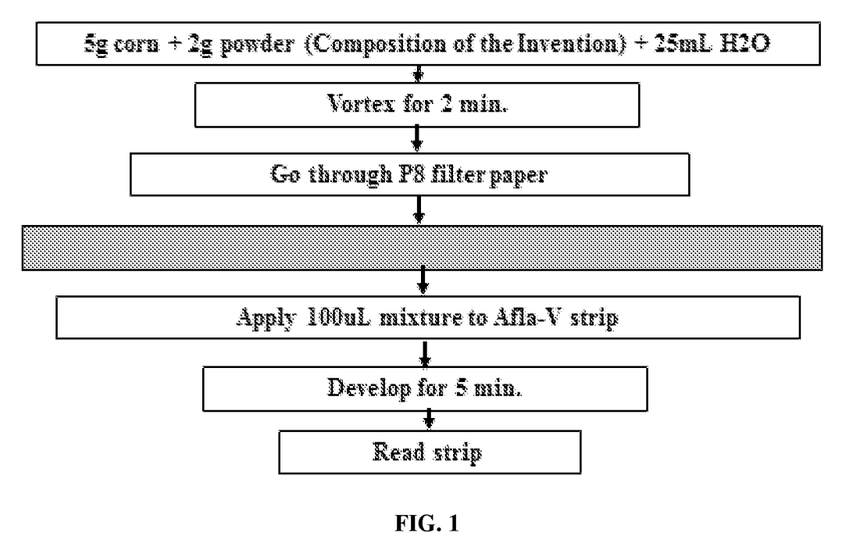
FIG. 1 illustrates an exemplary process of extracting and detecting aflatoxins according to an exemplary embodiment using a composition of the present invention.
Figure 2:
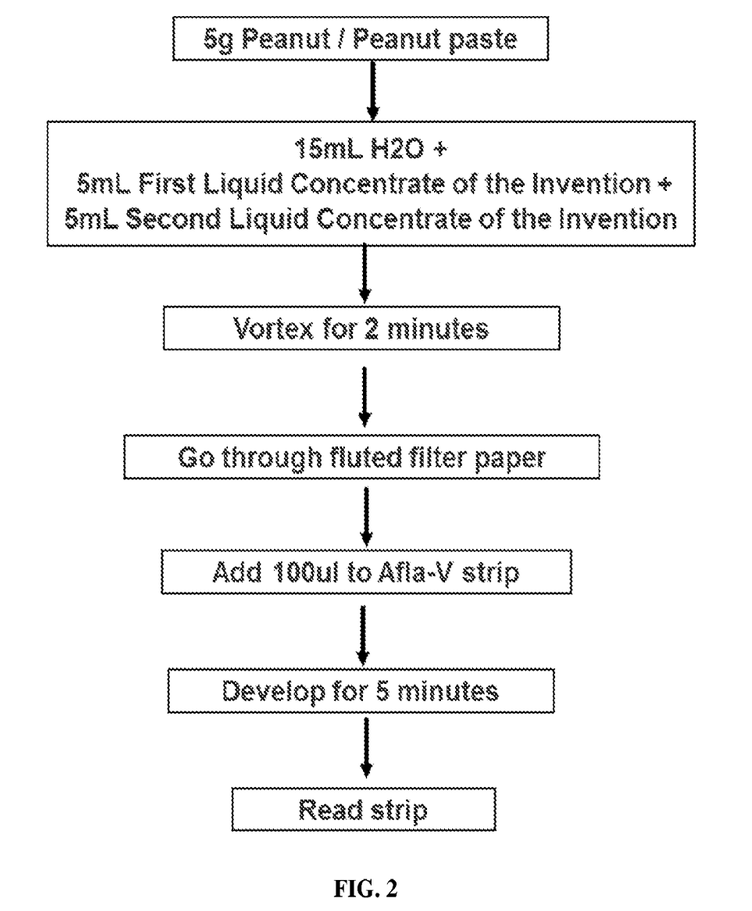
FIG. 2 illustrates an exemplary process of extracting and detecting aflatoxins according to an exemplary embodiment using a first and second concentrated liquid of the present invention.
Figure 3:
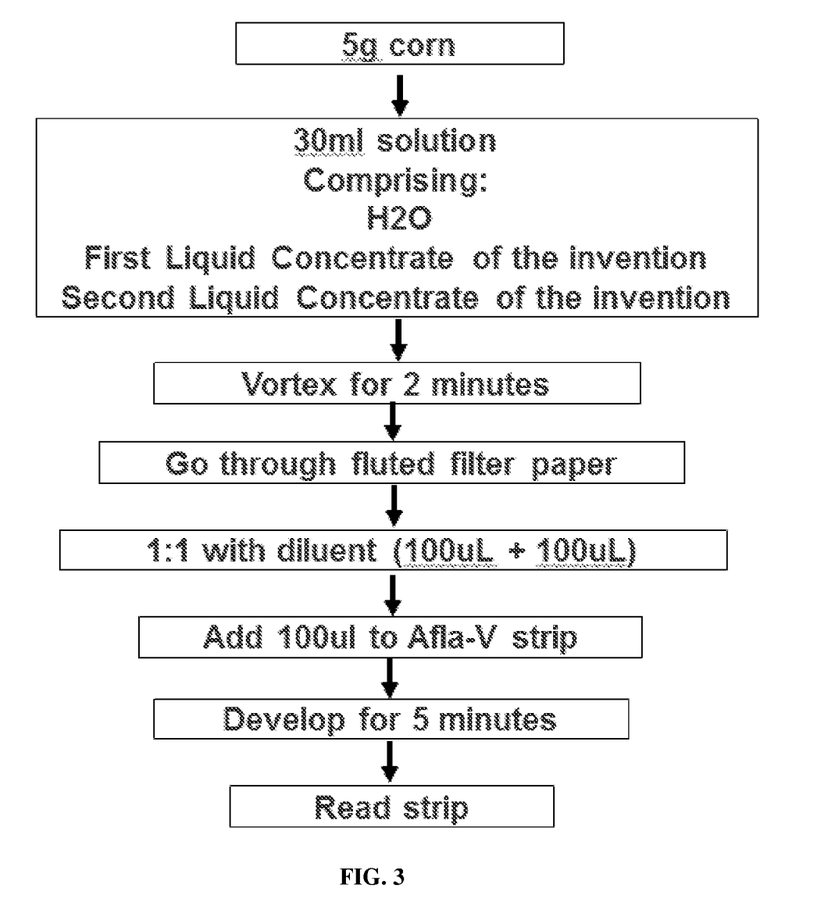
FIG. 3 illustrates another exemplary process of extracting and detecting aflatoxins according to an exemplary embodiment using a first and second concentrated liquid of the present invention.

The present invention provides a composition and a method which can be used for extracting and detecting mycotoxins from a sample without using hazardous organic solvents. Particularly, the composition of the invention may be optimized for the extractions of such mycotoxins in aqueous solution.

It is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about", when used in reference to a particular recited numerical value or range of values, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All publications mentioned herein are incorporated herein by reference in their entirety.

Definition

The term "mycotoxin", as used herein, is a toxic secondary metabolite produced by organisms of the fungi kingdom, commonly known as molds. The term 'mycotoxin' is usually applied to the toxic chemical products produced by fungi that readily colonize crops. One mold species may produce many different mycotoxins, and the same mycotoxin may be produced by several species The term "aflatoxin", as used herein, is a type of mycotoxin, which is produced by *Aspergillus flavus* and *Aspergillus parasiticus*. A variety of aflatoxins have been identified as aflatoxin types $B_1$, $B_2$, $G_1$, $G_2$, $M_1$ and $M_2$ Aflatoxin $B_1$ Aflatoxins occur naturally in peanuts, peanut meal, cottonseed meal, corn, dried chili peppers, and the like. Aflatoxins are a frequent contaminant of the human food supply in many areas of the world and are statistically associated with increased incidence of human liver cancer in Asia and Africa, in particular.

The term "sample", as used herein, refers to any mixtures of molecules that comprise at least one molecule that is subjected to extraction, detection, separation, analysis or profiling. Particular examples in the present invention include, but are not limited to, food samples such as produce or environmental samples. Particularly, the food samples may be produce or crops such as corn, peanuts, cotton or cottonseed, wheat, soybeans, rice, and the like. In certain exemplary embodiments, the samples may include a detectable range of mycotoxins such as aflatoxins.

As used herein, the term "surfactant" refers to a chemical compound which reduces a surface tension between two liquids or between a liquid and a solid. Surfactants may act as detergents, wetting agents, emulsifiers, foaming agents, dispersants and the like. In certain embodiments, the surfactants may be used to stabilize hydrophobic organic molecules, such as lipid, oil, aromatic compounds, hydrophobic proteins and the like, in an aqueous solution.

As used herein, the term "polymer" refers to a high molecular-weight molecule which contains repeating subunits and imparts specific properties to a solution. In certain embodiments of the present invention, the polymer may have a hydrophilic group, hydrophobic group or combined groups, and further may be used as a surfactant or a surface modifier.

As used herein, the term "viscosity modifier" refers to an ingredient in a solution to modulate the viscosity of the solution. The viscosity modifier may be particularly added to provide higher viscosity, surface tension or flowability. In addition, the viscosity modifier may have mild chemical activity in the solution. In certain embodiments, in aqueous solution, exemplary viscosity modifiers may be glucose, sucrose or cellulose, such that the viscosity or density of the solution may increase.

As used herein, the "buffering salt" refers to any types of salts which can be dissolved in water or aqueous solution and maintain buffering condition of the solution. The buffering salt generally includes salts, acidic salts, basic salts or combinations thereof. The buffering salt may not react with other components in the solution but influence on pH, buffering or electrolytic properties thereof.

The terms "analysis" or "analyzing" are used interchangeably and refer to any of the various methods of separating, detecting, isolating, purifying, solubilizing, detecting and/or characterizing small nutrient molecules (e.g., vitamins). Examples include, but are not limited to, solid phase extraction, solid phase micro extraction, electrophoresis, mass spectrometry, e.g., MALDI-MS or ESI, liquid chromatography, e.g., high performance, reverse phase, normal phase, or size exclusion, ion-pair liquid chromatography, liquid-liquid extraction, e.g., accelerated fluid extraction, supercritical fluid extraction, microwave-assisted extraction, membrane extraction, soxhlet extraction, precipitation, clarification, electrochemical detection, staining, elemental analysis, Edmund degradation, nuclear magnetic resonance, infrared analysis, flow injection analysis, capillary electrochromatography, ultraviolet detection, and combinations thereof.

The term "affinity chromatography", as used herein, refers to a method of separating chemical or biochemical species in a sample based on a highly specific interaction between substrate and the ligand. Particular examples of such specificity may be between antigen and antibody, between enzyme and substrate, or between receptor and ligand. In affinity chromatography, capturing molecules having specificity to analytes can be immobilized in the chromatographic material or resin in a column or diagnostic tool and the analytes of interest can be seized by the resin. In certain exemplary embodiments, aflatoxins can be recognized and captured by their specific antibodies immobilized in an affinity chromatography column or colloidal particles.

The term "test strip", as used herein, refers to a diagnostic strip or dipstick used for determining presence of analytes. Chemical or biochemical species which have specificity to analytes may be immobilized on colloidal particles and the analytes specifically bound to the particles on the strip may be detected and analyzed quantitatively or qualitatively. In certain exemplary embodiments, a test strip may include aflatoxin-specific antibodies for detecting aflatoxins in a sample.

Extraction of Mycotoxins

The present invention provides a novel extraction of mycotoxins without using organic solvents, and also discloses a composition which can be used for the extraction in aqueous solution.

In one aspect, disclosed is extraction of mycotoxins from a sample in aqueous solutions, whereby the use of organic solvent may be avoided. Accordingly, the composition and concentrated liquids of the invention may be used for efficiently extracting mycotoxins having high hydrophobicity. In particular, the composition may include surfactants or dispersants to solubilize or stabilize organic molecules in aqueous solution. In an exemplary embodiment, the composition may include one or more of surfactants, one or more of polymers, one or more of viscosity modifiers, one or more of buffering salts and the like.

Extracting, as used herein, is a chemical process to transfer chemical species from one phase to another phase, such as from organic solvent phase to aqueous phase. In certain exemplary embodiments, the mycotoxins in sample such as solid or oil phase can be transferred to aqueous liquid phase, such that detection can be performed. In an exemplary embodiment, aflatoxins may be transferred from the food sample and dissolved in water by use of the composition in the invention.

In certain embodiments, the extracting may be performed by generally known methods in the art. Exemplary extracting processes may be, but are not limited to, shaking, vortexing, ultrasonication, heat reflux, microwave-assisted extraction, controlled pressure drop extraction, and the like.

In certain exemplary embodiments, the mycotoxins to be extracted may be, but are not limited to, aflatoxin, fumonisin, ochratoxin, zearalenone and the like. Among those mycotoxins, aflatoxins may be effectively extracted and analyzed using the composition of the invention.

In certain exemplary embodiments, the sample may be a food or beverage sample, environmental sample, or biological sample, without limitation. The food sample may include produce, food products, and the like. Exemplary food samples may be, but not limited to, corn, maize, peanuts, cotton or cottonseed, wheat, soybeans, rice, dairy products, breakfast cereals, baby food, canned fruits, and related commodity food products. When the sample is provided as solid, the sample may be prepared appropriately and combined with the composition of the invention and water. When the sample is provided as aqueous liquid, the sample may be directly combined with the composition of the invention in a predetermined range thereof.

Composition

The present invention provides a composition or concentrated liquids for extracting mycotoxins included in a food sample. The composition or concentrated liquids particularly can be used for the method of extracting mycotoxins without using an organic solvent. According to various exemplary methods as described above, the composition may be combined with the sample including mycotoxins and water before analyzing the sample.

In one aspect, provided is the composition including: one or more of surfactants, one or more of polymers, one or more of viscosity modifiers, and one or more of buffering salts.

In another aspect, provided are concentrated liquids including one or more of surfactants, and one or more of buffering salts. In particular embodiments when concentrated liquids are used, the concentrated liquids do not contain polymers or viscosity modifiers Surfactant, as disclosed above, is used to modify the surface of analytes and consequently stabilizes the analytes. In certain embodiments, surfactant in the solution may include a hydrophilic group, a hydrophobic group or a combination thereof and accordingly, stabilize the analytes in aqueous environments. In certain exemplary embodiments, the surfactant may solubilize and stabilize aflatoxins which possess series of aromatic rings in their structure in water without any organic solvent. Accordingly, the dispersion or extraction of aflatoxins may be substantially improved by addition of surfactants.

In certain embodiments, the surfactants used in the invention may include a generally used chemical surfactant in the art. For example, polysorbate 20, sodium stearate, 4-(5-dodecyl) benzenesulfonate, sodium dodecyl sulfate (SDS), trimethylhexadecyl ammonium chloride and the like may be used in the present invention, but the examples may not be limited thereto.

In certain exemplary embodiments of the composition of the invention, the surfactant may be included in an amount of about 2 to 10 wt %, of about 3 to 9 wt %, of about 4 to 8 wt %, of about 5 to 7 wt %, of about 5.5 to 7.5 wt %, or particularly of about 6 wt %. In certain exemplary embodiments, the composition may include SDS as surfactant component.

In an exemplary embodiment, the composition may include SDS in an amount of about 6 wt %, based on the total weight of the composition.

In certain embodiments when the concentrated liquids of the invention are used, the first and second concentrated liquids include different surfactants. In certain other embodiments, the concentrated liquids use the same surfactants, optionally in addition to other surfactants. In certain exemplary embodiments, the first concentrated liquid includes a first surfactant which may be included in an amount of about 2.4 to 7.2 wt %, or particularly of about 4.8 wt %. In certain exemplary embodiments the second concentrated liquid includes a second surfactant which may be included in an amount of about 5 to 15% by volume. In certain exemplary embodiments, the concentrated liquids include SDS and polysorbate 20 as surfactant components.

In an exemplary embodiment, the first concentrated liquid includes SDS in an amount of about 4.8 wt %, based on the total weight of the concentrated liquid.

In an exemplary embodiment, the second concentrated liquid includes polysorbate 20 in an amount of about 10% by volume, based on the total volume of the concentrated liquid.

Polymer, as used herein, may be a water-soluble polymer and also be used as surfactant or surface modifier, which may modify the surface of analytes. In addition, the polymer may stabilize a buffering condition, such as pH or salt concentration.

In certain embodiments, the polymer is, but not limited to, polyacrylic acid, polyol, polyethylene glycol (PEG), or polyvinylpyrrolidone. In an exemplary embodiment, the composition may include polyethylene glycol (PEG). The PEG having an average molecular weight in a range of about 1,000 to about 40,000 may be included in the composition, or particularly, the PEG having an average molecular weight of about 6,000; 8,000; 10,000; 12,000; 14,000; 16,000; 18,000; 20,000; 22,000; 24,000; 26,000; 28,000; 30,000; 32,000 may be used. In certain exemplary embodiments, PEG having an average molecular weight of about 20,000 may be used.

In certain embodiments, the polymer may be included in an amount of about 30 to 50 wt %, of about 32.5 to 47.5 wt %, of about 35 to 45 wt %, of about 37.5 to 42.5 wt % or particularly of about 40 wt %, based on the total weight of the composition.

In an exemplary embodiment, the PEG 20,000 may be included in an amount of about 40 wt % in the composition, based on the total weight of the composition.

Viscosity modifier, as used herein, may stabilize an extracting solution when the composition of the invention is dissolved in water and stabilize the viscosity of the extracting solution in various temperature or pressure range. In certain embodiments, the viscosity modifier in the invention may be, but not limited to, a water-soluble organic polymer, cellulose, sucrose, glucose, or mannitol.

In certain embodiments, the viscosity modifier may be included in an amount of about 30 to 50 wt %, of about 32.5 to 47.5 wt %, of about 35 to 45 wt %, of about 37.5 to 42.5 wt % or particularly of about 40 wt %, based on the total weight of the composition.

In an exemplary embodiment, sucrose may be included in an amount of about 40 wt % in the composition, based on the total weight of the composition.

Buffering salt may be included in the composition to maintain buffering condition, salt concentration and pH of an extracting solution. In certain exemplary embodiments, the buffering salt may be a salt, an acidic salt, a basic salt or combinations thereof. In yet certain exemplary embodiments, the buffering salt may include, but is not limited to, sulfate, citrate, acetate, chloride, bromide, iodide, nitrate, bisulfate, phosphate, lactate, salicylate, acid citrate, tartrate, oleate, tannate, pantothenate, bitartrate, ascorbate, succinate, maleate, besylate, fumarate, gluconate, glucuronate, saccharate, formate, benzoate, glutamate, methanesulfonate, ethanesulfonate, benzenesulfonate, and p-toluenesulfonate salts and the like. Exemplary salts may be, but are not limited to, sodium chloride, sodium sulfate, sodium citrate, sodium acetate, sodium bromide, and sodium iodide, potassium chloride, potassium acetate, potassium bromide, potassium iodide and the like. Exemplary acidic salts may include, but are not limited to, sodium bicarbonate ($NaHCO_3$), sodium hydrosulfide (NaHS), sodium bisulfate ($NaHSO_4$), monosodium phosphate ($NaH_2PO_4$), disodium phosphate ($Na_2HPO_4$) and the like. Exemplary basic salts may be, but are not limited to, calcium carbonate, sodium carbonate, potassium cyanide, and the like.

In certain exemplary embodiments when the composition of the invention is used, the salt and/or acidic salt may be included, each respectively, in an amount of about 5 to 9 wt %, of about 6 to 8 wt %, of about 6.5 to 7.5 wt % or particularly of about 7 wt %. Alternatively, the total amount of salt and acidic salt in the compound may be in an amount of about 10 to 18 wt %, of about 11 to 17 wt %, of about 12 to 16 wt %, or of about 13 to 15 wt %. In an exemplary embodiment, sodium chloride (NaCl) and sodium dihydrogen phosphate ($NaH_2PO_4$) may be used in an amount of about 7 wt % respectively.

In certain exemplary embodiments when the concentrated liquids of the invention are used, the salt and/or acidic salt may be included, each respectively, in an amount of about 6 to 18 wt %, or particularly of about 12.4 wt %. Alternatively, the total amount of salt and acidic salt in the compound may be in an amount of about 1.4 to 4.2 wt %, In an exemplary embodiment, sodium chloride (NaCl) and sodium monohydrogen phosphate ($NaH_2PO_4$) may be used in an amount of about 12.4 wt % and 2.8 wt % respectively.

In certain exemplary embodiments, the pH of the extracting solution which is formed by combining the composition and water may be maintained by the salt and acidic salt in a range of about 4 to 9, of about 5 to 9, or particularly about 6-8 by addition of salt and acidic salt compounds.

According to an exemplary embodiment, the composition may include: poly ethylene glycol (PEG), sucrose, sodium chloride, sodium dihydrogen sulfate, and sodium dodecyl sulfate (SDS). Particularly, the composition may include: PEG in an amount of about 40 wt %, sucrose in an amount of about 40 wt %, NaCl in an amount of about 7 wt %, $NaH_2PO_4$ in an amount of about 7 wt %, and SDS in an amount of about 6 wt %.

According to an exemplary embodiment, the concentrated liquids may include: sodium chloride, sodium monohydrogen phosphate, polysorbate 20, and sodium dodecyl sulfate (SDS). Particularly, the composition may include: NaCl in an amount of about 12.8 wt %, $NaH_2PO_4$ in an amount of about 2.8 wt %, polysorbate 20 in an amount of 10 volume % and SDS in an amount of about 4.8 wt %.

In certain embodiments, other additives may be included in the composition to improve physical or chemical property of the composition, such as shelf-storage stability or solubility.

In certain exemplary embodiments, the composition may be a solid powder which can be mixed and dissolved with a sample in water or aqueous solution.

In other aspect, the composition and components thereof may be a powder or crystalline powder.

Method of Extracting Mycotoxins

The present invention provides methods of extracting and detecting mycotoxins from a sample. Particularly, methods of the invention include the use of the composition above and exclude the use of any organic solvent.

In one embodiment, the method of extracting may comprise steps of:
preparing a sample by combining the sample with a composition of the invention; and extracting mycotoxins from the prepared sample.

In certain embodiments, the composition used in the method may include one or more of surfactants, one or more of polymers, one or more of viscosity modifiers, one or more of buffering salts. In an exemplary embodiment, the composition may include: PEG in an amount of about 40 wt %, sucrose in an amount of about 40 wt %, NaCl in an amount of about 7 wt %, $NaH_2PO_4$ in an amount of about 7 wt %, and SDS in an amount of about 6 wt %.

In another embodiment, the method of extracting may comprise steps of:
preparing a sample by combining the sample with a first and second concentrated liquid of the invention and water; and
extracting mycotoxins from the prepared sample.

In certain embodiments, the first and second concentrated liquids used in the method may include one or more of surfactants, one or more of buffering salts. In an exemplary embodiment, the composition may include: NaCl in an amount of about 12.4 wt %, $NaH_2PO_4$ in an amount of about 2.8 wt %, Polysorbate 20 in an amount of 10 volume %, and SDS in an amount of about 10 volume %.

In the certain embodiments, the sample may be solid. In preparing the sample, the solid sample may be combined with the composition of the invention and water. In other certain embodiments, the sample may be liquid and the sample may be prepared by combining with the composition. In yet other embodiments, the prepared sample may be diluted to obtain detectable range of analytes included in the sample.

In certain embodiments, preparation of the sample may be performed at a temperature of about 10 to 30° C., or room temperature, at which temperature the composition and the analytes, i.e. mycotoxins, may not be altered or deteriorate.

In certain embodiments, the analytes in the sample may be extracted by any methods in the art. The method may include, but is not limited to, shaking, vortexing, ultrasonication, heat reflux, microwave-assisted extraction, controlled pressure drop extraction, and the like. In an exemplary embodiment, the analytes in the sample may be extracted by vortexing after combining the sample with the composition. Exemplary vortexing may be performed at least about 2 min.

In certain embodiments, the method may further comprise filtering the prepared sample. In certain exemplary embodiments, any general method of filtering in the art may be used in the method of the invention. In certain exemplary embodiments, the filtering may be, but is not limited to, vacuum filtering, gravity filtering and the like. The filtering may also be performed with, but not limited to, filter paper, membrane, or adsorbent.

In yet certain embodiments, the method may further comprise analyzing the mycotoxins from the sample. In certain exemplary embodiments, the analyzing may be performed after sample preparation using affinity chromatography. The analysis may use, but is not limited to, analytical chromatography columns such as liquid chromatography, high performance liquid chromatography (HPLC), reverse phase liquid chromatography, test strip, and the like. In particular, affinity chromatography columns or test strips may comprise affinity resin or species such as antibody, ligands, or chemical species having specificity toward mycotoxins.

In an exemplary embodiment, a test strip comprising antibodies specific to aflatoxins may be used for detecting and analyzing aflatoxins in the prepared samples. It is appreciated that Afla-V® strip test (VICAM, Milford, MA) provides a range of options for method development in the invention.

In certain embodiments, the method may further comprise quantitating a level of the mycotoxins in the sample. The mycotoxins may be detected by the test strip and test strip reader or by the affinity chromatography columns whereby the column eluate may be analyzed by, but not limited to, use of a fluorometer. It is appreciated that VICAM Series 4 EX fluorometer (VICAM, Milford, MA) provides a range of options for method development in the invention.

In an exemplary embodiment, the level of mycotoxins may be quantitated by measuring the fluorescence of chemical species at a wavelength of about 454 nm in a single-cell fluorometer.

In other embodiments, the methods may further include calibrating the detected level of the mycotoxins.

Example 1

Materials and Reagent

Materials and reagents (e.g. PEG 20,000, Sucrose, NaCl, $Na_2HPO_4$, SDS) were purchased commercially from Sigma Aldrich Co., St. Louis, MO or JT Baker/Avantor Performance Materials, Inc., Center Valley, PA Composition A composition is prepared by combining PEG 20,000 in an amount of about 40 wt %, sucrose in an amount of about 40 wt %, sodium chloride (NaCl) in an amount of about 7 wt %, sodium dihydrogen phosphate ($Na_2HPO_4$) in an amount of about 7 wt %, and SDS in an amount of about 6 wt %.

Extraction and Assay

Fine milled corn reference samples from Trilogy Laboratories for which aflatoxin levels were determined by HPLC were tested. The corn sample (5 g) was combined with 2 g of the composition and 25 mL of distilled water. The mixture was vortexed for about 2 minutes and filtered using a filter paper to remove solid debris from the sample. The liquid filtrate was obtained as an extract for analysis.

The extract of about 100 μL in volume was applied to an AFLA-V® strip and the strip was developed for about 5 min. Level of aflatoxin was determined using the Vertu strip test reader (VICAM, Milford, MA). The samples were run in triplicate.

Result

Each level of aflatoxin concentration was measured in three replicates. Individual data points, means and % coefficient of variability are presented in the table below.

| Sample | ppb | Mean (ppb) | Standard Deviation | % CV (coefficient of variability) | HPLC detection |
|---|---|---|---|---|---|
| 1 QC corn | 1.3 0.0 0.0 | 0.4 | 0.7 | 173 | 0 ppb |
| 2 AC287 | 5.3 5.6 6.0 | 5.6 | 0.4 | 6 | 5.4 ppb |
| 3 MTC9991 | 8.3 8.8 7.5 | 8.2 | 0.6 | 8 | 8.4 ppb |
| 4 MTC9993 | 14.9 15.3 15.5 | 15.2 | 0.3 | 2 | 17.4 ppb |
| 5 AC241 | 21.4 21.5 22.3 | 21.7 | 0.5 | 2 | 21.2 ppb |
| 6 AC279 | 65.8 74.0 88.3 | 76.0 | 11.4 | 15 | 99.9 ppb |

The above results show acceptable precision and accuracy at 5 ppb, 10 ppb, and 20 ppb in comparison with GIPSA requirements. Thus, the present invention provides a convenient and accurate extraction and detection methods of aflatoxins in a range of about 0 to 100 ppb.

Example 2

Materials and Reagent

Materials and reagents (e.g. PROCLIN 300 (TM, Supelco), Tween 20, Sucrose, NaCl, $Na_2HPO_4$, SDS) were purchased commercially from Sigma Aldrich Co St. Louis, MO First Concentrated Solution A first concentrated solution was prepared by combining 900 ml purified water, 48 grams of SDS, and 5 mL; of ProClin300 in a 1 L vessel. The mixture was stirred until all chemicals were dissolved in the solution. The final volume was brought to 1 L by addition of more purified water.

Second Concentrated Solution

A second concentrated solution was prepared by combining 800 mL of purified water, 124 grams of NaCl, 28 grams of $Na_2HPO_4$, 100 mL of Tween20 and 5 mL of ProClin300 in a 1 L vessel. The mixture was stirred until all chemicals were dissolved in the solution. The final volume was brought to 1 L by addition of more purified water.

Extraction and Assay

Three Peanut Paste samples from Trilogy Laboratories for which aflatoxin levels were determined by HPLC were tested. [A-PP-5 having 5 ppb peanut; A-PP-10 having 10 ppb peanut; and A-PP-21 having 21 ppb peanut]. In each case, the peanut sample (5 g) was first combined with 15 mL of distilled water. Then 5 mL of the first concentrated solution, and 5 mL of the second concentrated solution were added to the mixture. The mixture was vortexed for about 2 minutes and filtered using a filter paper to remove solid debris from the sample. The liquid filtrate was obtained as an extract for analysis.

The extract of about 100 μL in volume was applied to an AFLA-V® strip and the strip was developed for about 5 min. Level of aflatoxin was determined using the Vertu strip test reader (VICAM, Milford, MA). The samples were run in triplicate.

Materials and Reagent

Materials and reagents (e.g. PROCLIN 300 (TM, Supelco), Tween 20, NaCl, $Na_2HPO_4$, SDS) were purchased commercially from Sigma Aldrich Co St. Louis, MO First Concentrated Solution A first concentrated solution was prepared by combining 900 ml purified water, 48 grams of SDS, and 5 m; of ProClin300 in a 1 L vessel. The mixture was stirred until all chemicals were dissolved in the solution. The final volume was brought to 1 L by addition of more purified water.

Second Concentrated Solution

A second concentrated solution was prepared by combining 800 mL of purified water, 124 grams of NaCl, 28 grams of $Na_2HPO_4$, 100 mL of Tween20 and 5 mL of ProClin300 in a 1 L vessel. The mixture was stirred until all chemicals were dissolved in the solution. The final volume was brought to 1 L by addition of more purified water.

Extraction and Assay

Three peanut paste samples from Trilogy Laboratories for which aflatoxin levels were determined by HPLC were tested. [C-PP-5 having 5 ppb paste; C-PP-10 having 10 ppb paste; and C-PP-20 having 20 ppb paste; In each case, the peanut sample (5 g) was first combined with 15 mL of distilled water. Then 5 mL of the first concentrated solution, and 5 mL of the second concentrated solution were added to the mixture. The mixture was vortexed for about 2 minutes and filtered using a filter paper to remove solid debris from the sample.

The filtered extract of about 100 μL in volume was applied to an AFLA-V® strip and the strip was developed for about 5 min. Level of aflatoxin was determined using the Vertu strip test reader (VICAM, Milford, MA). The samples were run in triplicate.

Result

Each level of aflatoxin concentration was measured in three replicates. Individual data points, means and % coefficient of variability are presented in the table below.

| Sample | HPLC (ppb) | T/C | ppb | Mean (ppb) | SD | % CV |
|---|---|---|---|---|---|---|
| A-PP-5 | 5 | 9.47 13.98 12.54 | 6.7 4.1 4.8 | 5 | 0.26 | 23 |
| A-PP-10 | 10 | 6.34 | 9.8 | 10 | 0.04 | 1 |

| Sample | HPLC (ppb) | T/C | ppb | Mean (ppb) | SD | % CV |
|---|---|---|---|---|---|---|
| | | 6.33 | 9.8 | | | |
| | | 6.83 | 9.2 | | | |
| C-PP-20 | 20 | 2.27 | 20.0 | 22 | 0.98 | 10 |
| | | 2.15 | 22.9 | | | |
| | | 2.43 | 20.9 | | | |

The above results show acceptable precision and accuracy at 5 ppb, 10 ppb, 20 ppb, in comparison with GIPSA requirements. Thus, the present invention provides a convenient and accurate extraction and detection methods of aflatoxins.

Materials and Reagent

Materials and reagents (e.g. PROCLIN 300 (TM, Supelco), Tween 20, Sucrose, NaCl, $Na_2HPO_4$, SDS) were purchased commercially from Sigma Aldrich Co St. Louis, MO First Concentrated Solution A first concentrated solution was prepared by combining 900 ml purified water, 48 grams of SDS, and 5 m; of ProClin300 in a 1 L vessel. The mixture was stirred until all chemicals were dissolved in the solution. The final volume was brought to 1 L by addition of more purified water.

Second Concentrated Solution

A second concentrated solution was prepared by combining 800 mL of purified water, 124 grams of NaCl, 28 grams of $Na_2HPO_4$, 100 mL of Tween20 and 5 mL of ProClin300 in a 1 L vessel. The mixture was stirred until all chemicals were dissolved in the solution. The final volume was brought to 1 L by addition of more purified water.

Extraction and Assay

Five finely milled corn samples from Trilogy Laboratories for which aflatoxin levels were determined by HPLC were tested. In each case, the corn sample (5 g) was first combined with 15 mL of distilled water. Then 5 mL of the first concentrated solution, and 5 mL of the second concentrated solution were added to the mixture. The mixture was vortexed for about 2 minutes and filtered using a filter paper to remove solid debris from the sample. The liquid filtrate was obtained and diluted 1:1 with Afla-V diluents as an extract for analysis.

The diluted extract of about 100 μL in volume was applied to an AFLA-V® strip and the strip was developed for about 5 min. Level of aflatoxin was determined using the Vertu strip test reader (VICAM, Milford, MA). The samples were run in triplicate.

Result

Each level of aflatoxin concentration was measured in three replicates. Individual data points, means and % coefficient of variability are presented in the table below.

| ID | T/C | ppb | Mean (ppb) | HPLC (ppb) |
|---|---|---|---|---|
| C1 | 19.43 | 2.1 | 1.6 | <1 |
| | 24.30 | 0.1 | | |
| | 17.95 | 2.6 | | |
| C2 | 8.56 | 7.4 | 7.0 | 5.4 |
| | 9.61 | 6.6 | | |
| | 9.06 | 7.0 | | |
| C3 | 5.02 | 12.0 | 11.8 | 11 |
| | 5.11 | 11.8 | | |
| | 5.24 | 11.5 | | |
| C4 | 2.45 | 20.8 | 21.4 | 21.2 |
| | 2.36 | 21.4 | | |
| | 2.26 | 22.0 | | |
| C5 | 0.53 | 62.0 | 52.3 | 50.8 |
| | 0.78 | 47.0 | | |
| | 0.76 | 47.9 | | |

Throughout this application, various publications, including United States patents, are referenced by author and year and patents by number. The disclosures of these publications and patents in their entireties are hereby incorporated by reference into this application.

The present inventions have been described in detail including preferred embodiments thereof. However, it should be appreciated that those skilled in the art, upon consideration of the present disclosure, may make modifications and improvements within the spirit and scope of the present inventions.

What is claimed is:

1. A liquid concentrate effective for extracting mycotoxins in a sample, comprising: an effective amount of one or more of surfactants selected from the group consisting of sodium dodecyl sulfate (SDS) and polysorbate 20; and an effective amount of buffering salts consisting of sodium chloride and disodium phosphate ($Na_2HPO_4$);

wherein the effective amount of the one or more surfactants ranges from about 2.4 to 7.2 wt % and the effective amount of each of the buffering salts ranges from about 6 to 18 wt %, or wherein the effective amount of the one or more surfactants ranges from about 5 to 15% by volume and the effective amount of each of the buffering salts ranges from about 6 to 18 wt %.

2. The liquid concentrate of claim 1, wherein the one or more surfactants comprise about 2.4 to 7.2 wt % sodium dodecyl sulfate (SDS).

3. The liquid concentrate of claim 1, wherein the one or more surfactants are included from about 2.4 to 7.2 wt %.

4. The liquid concentrate of claim 1, wherein the one or more surfactants comprise sodium dodecyl sulfate (SDS).

5. The liquid concentrate of claim 1, comprising about 6 wt % sodium dodecyl sulfate (SDS), about 7 wt % sodium chloride (NaCl), and about 7 wt % disodium phosphate ($Na_2HPO_4$).

6. The liquid concentrate of claim 1, wherein the one or more surfactants are included from about 5 to 15% by volume.

7. The liquid concentrate of claim 6, wherein the one or more surfactants comprise polysorbate 20.

8. The liquid concentrate of claim 6, comprising polysorbate 20 at about 10 volume %, sodium chloride at about 12.4 wt %, and disodium phosphate at about 2.8 wt %.

* * * * *